United States Patent [19]

Subramanyam et al.

[11] Patent Number: 5,310,508

[45] Date of Patent: May 10, 1994

[54] MILD PERSONAL CLEANSING COMPOSITIONS CONTAINING SODIUM ALCOHOL ETHOXY GLYCERYL SULFONATE

[75] Inventors: Ravi Subramanyam, North Brunswick; Ben Gu, East Brunswick; Amrit Patel, Dayton; Jairajh Mattai, Metuchen; Clarence Robbins, Martinsville; Jane Clarke, Matawan; Tanya Clifton, Nutley, all of N.J.

[73] Assignee: Colgate-Palmolive Company, Piscataway, N.J.

[21] Appl. No.: 65,134

[22] Filed: May 19, 1993

Related U.S. Application Data

[63] Continuation-in-part of Ser. No. 914,369, Jul. 15, 1992, abandoned.

[51] Int. Cl.$^5$ .................. C11D 3/12; C11D 1/18; C11D 9/30
[52] U.S. Cl. .................. 252/549; 252/554; 252/546; 252/544; 252/117; 252/121
[58] Field of Search ............ 252/117, 121, 544, 546, 252/547, 552, 554, 549; 562/30, 108, 110, 111

[56] References Cited

U.S. PATENT DOCUMENTS

| | | |
|---|---|---|
| Re. 30,641 | 6/1981 | Verdicchio et al. ............... 252/526 |
| 2,674,580 | 4/1954 | Henkin ............................. 252/117 |
| 2,678,921 | 5/1954 | Turck ............................... 252/161 |
| 2,877,185 | 3/1959 | Krumrei et al. ................... 252/137 |
| 2,877,186 | 3/1959 | Krumrei ........................... 252/138 |
| 2,970,963 | 2/1961 | Walker et al. .................... 252/153 |
| 2,970,964 | 2/1961 | Krumrei et al. ................... 252/161 |
| 2,970,965 | 4/1961 | Parran et al. ..................... 252/137 |
| 2,988,511 | 6/1961 | Mills et al. ....................... 252/121 |
| 2,989,547 | 6/1961 | Whyte .............................. 260/348 |
| 3,024,273 | 3/1962 | Whyte et al. ..................... 260/513 |
| 3,102,893 | 9/1963 | Gaertner ........................... 260/348 |
| 3,179,599 | 4/1965 | Eaton et al. ...................... 252/153 |
| 3,243,455 | 3/1966 | Pizzini et al. ..................... 260/513 |
| 3,798,179 | 3/1974 | Hellyer ............................. 252/535 |
| 3,849,548 | 11/1974 | Grand .............................. 424/70 |
| 3,980,769 | 9/1976 | Ghilardi et al. ................... 424/70 |
| 3,996,147 | 12/1976 | Tarason ............................ 252/142 |
| 4,001,394 | 1/1977 | Fogel et al. ....................... 424/70 |
| 4,009,256 | 2/1977 | Nowak, Jr. et al. ............... 424/70 |
| 4,048,301 | 9/1977 | Papantoniou ..................... 424/70 |
| 4,061,602 | 12/1977 | Oberstar et al. .................. 252/547 |
| 4,075,131 | 2/1978 | Sterling ............................ 252/542 |
| 4,133,779 | 1/1979 | Hellyer et al. .................... 252/547 |
| 4,148,762 | 4/1979 | Koch et al. ....................... 252/544 |
| 4,180,470 | 12/1979 | Tokosh et al. .................... 252/121 |
| 4,186,113 | 1/1980 | Verdicchio et al. ............... 252/526 |
| 4,217,296 | 8/1980 | Berkowitz ........................ 260/458 |
| 4,244,840 | 1/1981 | Straw ............................... 252/540 |
| 4,329,334 | 5/1982 | Su et al. ........................... 424/70 |
| 4,343,726 | 8/1982 | Egan et al. ........................ 252/547 |
| 4,379,080 | 4/1983 | Murphy ........................... 252/526 |
| 4,414,144 | 11/1983 | Liebowitz et al. ................ 252/548 |
| 4,426,310 | 1/1984 | Verunica .......................... 252/106 |

(List continued on next page.)

FOREIGN PATENT DOCUMENTS

| | | |
|---|---|---|
| 9109924 | 7/1991 | PCT Int'l Appl. . |
| 9109931 | 7/1991 | PCT Int'l Appl. . |
| 9113958 | 9/1991 | PCT Int'l Appl. . |
| 2240111 | 1/1991 | United Kingdom . |

*Primary Examiner*—Paul Lieberman
*Assistant Examiner*—Necholus Ogden
*Attorney, Agent, or Firm*—Martin B. Barancik; Robert C. Sullivan

[57] ABSTRACT

A personal cleansing composition includes a salt, preferably sodium salt, of alcohol ethoxy glyceryl sulfonate. The preferred sodium salt of alcohol ethoxy glyceryl sulfonate has the formula:

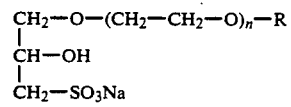

where R is a radical with 4 to 24 carbon atoms and n is a number from 1 to 10. The composition may take the form of a bar, combar, syndet bar, shampoo, liquid soap, bubble bath or shower gel.

30 Claims, No Drawings

U.S. PATENT DOCUMENTS

| | | | |
|---|---|---|---|
| 4,491,539 | 1/1985 | Hoskins | 252/541 |
| 4,502,538 | 3/1985 | Wellington et al. | 166/252 |
| 4,514,444 | 4/1985 | Ives et al. | 427/242 |
| 4,536,318 | 8/1985 | Cook et al. | 252/174.17 |
| 4,554,098 | 11/1985 | Klisch et al. | 252/547 |
| 4,561,998 | 12/1985 | Wertz et al. | 252/547 |
| 4,578,216 | 3/1986 | Fujii et al. | 252/542 |
| 4,636,329 | 1/1987 | Steuri | 252/106 |
| 4,673,525 | 6/1987 | Small et al. | 252/108 |
| 4,678,606 | 7/1987 | Akhter et al. | 252/542 |
| 4,704,272 | 11/1987 | Oh et al. | 424/70 |
| 4,731,201 | 3/1988 | Robbins et al. | 252/551 |
| 4,733,727 | 3/1988 | Falls | 252/8.554 |
| 4,736,795 | 4/1988 | Karas | 252/8.554 |
| 4,772,424 | 9/1988 | Greeb | 252/546 |
| 4,788,006 | 11/1988 | Bolich, Jr. et al. | 252/550 |
| 4,799,547 | 1/1989 | Borchardt | 252/8.554 |
| 4,812,253 | 3/1989 | Small et al. | 252/132 |
| 4,820,447 | 4/1989 | Medcalf, Jr. et al. | 252/117 |
| 4,832,872 | 5/1989 | Scandel | 252/547 |
| 4,842,850 | 6/1989 | Vu | 424/70 |
| 4,856,589 | 8/1989 | Kuhlman et al. | 252/8.554 |
| 4,863,618 | 9/1989 | Falls | 252/8.554 |
| 4,874,538 | 10/1989 | Dawson et al. | 252/117 |
| 4,877,546 | 10/1989 | Lai | 252/174.17 |
| 4,898,690 | 2/1990 | Bitter et al. | 252/554 |
| 4,919,838 | 4/1990 | Tibbetts et al. | 252/117 |
| 4,954,281 | 9/1990 | Resch | 252/107 |
| 5,002,680 | 3/1991 | Schmidt et al. | 252/90 |
| 5,076,953 | 12/1991 | Jordan et al. | 252/108 |
| 5,084,212 | 1/1992 | Farris et al. | 252/554 |
| 5,108,640 | 4/1992 | Schwartz et al. | 252/89 |

MILD PERSONAL CLEANSING COMPOSITIONS CONTAINING SODIUM ALCOHOL ETHOXY GLYCERYL SULFONATE

This application is a continuation-in-part application of U.S. Ser. No. 07/914,369 filed Jul. 15, 1992, now abandoned.

FIELD OF THE INVENTION

This invention relates generally to personal cleansing compositions which have reduced skin irritancy potential and superior cleaning ability. In particular, the invention relates to bars combination soap bars, shampoos, liquid soaps, shower gels, bubble baths and other personal cleansing products containing an anionic surfactant.

BACKGROUND OF THE INVENTION

The use of synthetic surfactants in cleansing products is well known. For example, U.S. Pat. Nos. 2,970,963, 2,970,964, 2,979,465, 2,988,511, 2,989,547, and 2,999,068 disclose the incorporation of alkyl glycerol ether sulfonates (AGES) in cleansing products such as household dishwashing detergent, cream shampoo and detergent bars. The formula for AGES is:

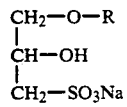

where $R = C_8 - C_{20}$.

It is known to use AGES in shampoos and soaps, as evidenced by U.S. Pat. Nos. 3,247,121, 3,980,769, 4,217,296, 4,244,840, 4,327,334, 4,491,539, 4,491,539, 4,636,329, and 4,678,606. Furthermore, U.S. Pat. No. 2,999,068 to Pilcher teaches that ethylene oxide polymers can be added to an AGES composition to provide lubricity to the lather of a soap bar. Also U.S. Pat. No. 4,554,098 to Klisch teaches that polyethylene oxide may be added to liquid detergents (e.g., sulfonates) to reduce skin irritation.

The prior art also teaches the use of ethoxylated surfactants. For example, U.S. Pat. No. 4,578,216 to Fujii teaches the use in shampoos of "polyoxyalkylene alkyl ether sulfates" having the formula:

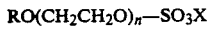

where X may be Na. Also U.S. Pat. No. 5,028,353, entitled "Combination Detergent and Soap Bar", assigned to the assignee of the present application, teaches the use of AEOS (alpha ethoxy olefin sulfonate) in soap bars. Finally, U.S. Pat. No. 4,877,546 to Lai, assigned to the assignee of the present application, discloses a surfactant system useful in hard surface cleansing systems comprising "alkyl ethenoxy ether sulfate" having the same formula: $RO(CH_2CH_2O)_n - SO_3X$.

However, ethoxylated surfactants are not readily processable into soap bars at high levels. For example bars with even as low as 2-3 wt % ethoxylated surfactant usually present processing problems. Generally 2-5 wt % ethoxylated surfactants present very significant problems and where such bar can be produced it is often of a soft and sticky nature.

None of the above-discussed prior art discloses the use of the sodium salt of alcohol ethoxy glyceryl sulfonate (manufactured under the trade name NEGS from Shell Chemical Company) in a cleansing product for human use. A patent which discloses the use of NEGS, i.e., U.S. Pat. No. 4,502,538 to Wellington, relates to the recovery of oil underground.

Fatty acid soaps have been widely employed and known for many years as effective general all purpose cleaning agents. However, the use of fatty acid soaps with hard water gives rise to the formation and precipitation of insoluble fatty acid salts commonly referred to as lime soaps. These precipitated lime soaps tend to coagulate and form a curd in wash basins, bath tubs and the like where the lime curd rises to the surface of the water and adheres to the wash basin or bath tub in the area of the water line. It is this precipitation and attachment of lime soaps to wash basin and bath tubs that produces the familiar ring on bath and basin surfaces. These lime soaps may also leave a film and a feeling of tightness on the skin after washing in hard water with fatty acid soaps. Consequently, various efforts have been undertaken to solve the lime soap curd formation by adding curd dispersants or using synthetic surfactants in place of all or part of the fatty acid soap.

The use of synthetic surfactants in place of fatty acid soaps eliminates the need for a dispersant because no lime soap curds will be formed by the synthetic surfactant in hard water. However, synthetic surfactants are more expensive than fatty acid soaps and synthetic surfactants can be irritating to the skin. By the term mild, it is meant the skin feel of the soap both during and after usage. The problem results from various groups on the surfactants forming salt-like linkages with the epidermis of the skin. Owing to this, the outer layers of the epidermis lose their elasticity, becoming cracked and prematurely rubbed off, which causes a sticky, stretched or burning sensation in the skin of the persons affected and leads to itching. It is also a factor that when a soap bar is comprised completely of a surfactant with no fatty acid soap, it is difficult to form the composition into bars.

Further, surfactants will tend to absorb moisture, swell and have a tendency to crack.

There are yet other properties that are necessary for a good soap composition. Besides being mild and not forming lime soap curd, the soap should also exhibit good lather performance. The use of anionic surfactants can yield a high lather volume, but again such surfactants have a fairly high degree of harshness with resulting skin irritation. When anionic surfactants are utilized, efforts to decrease the degree of harshness consist of adding to the soap composition substances such as moisturizers and fatty acids. However, these various additives then present other problems. When fatty acids are added to the soap compositions, there then results the potential problem of rancidity of the soap composition during a period of extended storage. The use of moisturizers can also create problems. For instance, moisturizers can leave the skin with a greasy filmy feeling as the skin dries. Such a skin feeling is opposite to that which is normally associated with clean skin.

The problem of reducing skin irritation also applies to other skin cleansing products, such as shampoos, liquid soaps, bubble baths and shower gels, containing anionic surfactants.

SUMMARY OF THE INVENTION

There is a personal cleansing composition comprising in solid or liquid form an anionic surfactant heretofore not disclosed for such use.

One object of the present invention is to improve upon the prior art personal cleansing products containing anionic surfactants by incorporating an anionic surfactant that reduces skin irritation.

Another object of the invention is to provide novel cleansing compositions that can be utilized in hard water, have good lather performance and are less harsh to the skin.

It is yet another object of the invention to provide soap/synthetic surfactant formulations which have mildness and sensorial attributes which are superior to those of conventional soap.

Another object of the invention is to provide detergent combar compositions which exhibit clinically assessed mildness and rinsability benefits relative to conventional soap.

A further object of the invention is to use a synthetic surfactant in combination with soap which can be processed easily in conventional soap equipment and has improved foam attributes.

Also it is an object of the invention to provide milder shampoos, liquid soaps, bubble baths and shower gels which retain a high level of cleaning.

Another object of the invention is to develop novel shampoo, liquid soap, bubble bath and shower gel compositions with a mild synthetic surfactant used in conjunction with non-ionic, amphoteric and anionic surfactants, gums and polyquaterniums.

The foregoing objects are attained in accordance with the invention by providing a personal cleansing composition comprising a salt, preferably sodium salt, of alcohol ethoxy glyceryl sulfonate. The preferred sodium salt of alcohol ethoxy glyceryl sulfonate has the formula:

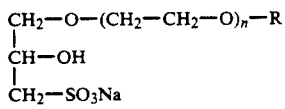

where R is the aliphatic radical or mixed aliphatic radicals with 4 to 24 carbon atoms and n is a number from 1 to 10. This salt is a non-tacky, high-melting-point, stable solid surfactant which can be processed easily in conventional soap equipment and has improved foam attributes.

In accordance with the preferred embodiments of the invention, this composition may take the form of a bar, combar, syndet bar, shampoo, liquid soap or detergent, bubble bath shower gel, or a cleansing composition with no soap.

A first preferred embodiment is a composition comprising the salt of alcohol ethoxy glycerol sulfonate in a cleansing composition. Soap or a further detergent surfactant may be present but need not be. Additional materials which can also be present alone or in various combinations include fragrance, skin conditioner, sodium chloride, germacide, colors and the like.

In accordance with the second preferred embodiment of the invention, a combar comprises 1 to 50 wt. % sodium salt of alcohol ethoxy glyceryl sulfonate and 1 to 85 wt. % soap, preferably 5 to 75 wt %. Preferably the soap is of the sodium tallowate, sodium cocoate and/or sodium palm kernelate types, although other types of soap can be used. Other additives include water, coconut and/or palm kernel acid, stearic acid, fragrance, skin conditioners, sodium chloride, germicide and colors.

In accordance with a third preferred embodiment, syndet bars can be made having a composition including other anionic surfactants in the range of 0-60 wt. %, such as sodium cocomonoglyceride sulfate or sodium cocoyl isethionate, with total surfactnat level in the range of 40-70 wt. %.

It has been found that the use of alcohol ethoxy glyceryl sulfonate surfactant results in a soap composition with a mildness factor significantly greater than the mildness of the saponified fatty acid component. Furthermore, alcohol ethoxy glyceryl sulfonate surfactant is more effective in reducing soap irritancy than other anionic surfactants used in commercial products. In addition, the soap composition can contain other adjuvants such as perfumes, titanium dioxides and the like.

In these soap compositions, the ratio of tallow fatty acid to coconut oil fatty acid can range from about 40% to about 90% saponified tallow fatty acid and from about 10% to about 60% saponified coconut oil fatty acid.

Through the use of these soap compositions, there results a mild bar which has good lathering characteristics and negligible skin irritancy.

In accordance with the fourth preferred embodiment of the invention, the shampoo composition comprises 2 to 25 wt. % sodium salt of alcohol ethoxy glyceryl sulfonate and one or more of the following ingredients: non-ionic cocodiethanolamide, anionic shampoo surfactants, gums, amphoterics and polyquaterniums. Other additives include fragrance, sodium chloride, germicide and colors.

In accordance with the fifth preferred embodiment of the invention, the liquid soap or bubble bath comprises 2 to 25 wt. % sodium salt of alcohol ethoxy glyceryl sulfonate and one or more of the additional ingredients, mentioned in the previous paragraph, which are incorporated in the composition of the second preferred embodiment.

In accordance with the sixth preferred embodiment of the invention, the shower gel comprises 2 to 25 wt. % sodium salt of alcohol ethoxy glyceryl sulfonate and one or more of the aforementioned additional ingredients.

DETAILED DESCRIPTION OF THE PREFERRED EMBODIMENTS

In accordance with a preferred embodiment of the invention, a mild skin cleansing combar comprises 1 to 50 wt. % of a surfactant having the formula:

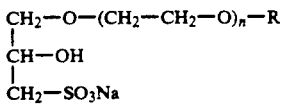

where R is the aliphatic radical or mixed aliphatic radicals with 4 to 24 carbon atoms and n is a number from 1 to 10, and further comprising 5 to 75 wt. % of a soap. The preferred surfactants are sodium salts of alcohol ethoxy glyceryl sulfonate. The preferred sodium salt of alcohol ethoxy glyceryl sulfonate is manufactured by Shell Chemical Company under the trade name NEGS- 23, in which R is an alkyl group of 12 and 13 carbon atoms and the average value of n=1 to 3 ethylene oxide units. Alternatively, NEGS-45 can be used, in which R is an alkyl group of 14 and 15 carbon atoms and the average value of n=1 to 3 ethylene oxide units. N is most preferably an average value of 1.

Although referred to throughout the specification and examples as the salt (sodium) of alcohol ethoxy glyceryol sulfonate, (NEGS) the material is not pure NEGS due to the process of making ethoxylated materials. The actual ethoxylated salt is only about 50–60 wt % of the material. The remainder of the material is the non ethoxylated salt. Depending upon the process employed, higher purities can be obtained. A typical distribution of ethoxyl groups in the NEGS employed in the specification examples is provided below:

| Ethylene oxide (EO) distribution of alkyl ethoxylated alcohol glyceryl sulfonate | | |
|---|---|---|
| EO# | NEGS-23, % WT | NEGS 45, % WT |
| 0 | 49 | 42 |
| 1 | 19 | 22 |
| 2 | 13 | 15 |
| 3 | 7 | 8 |
| 4 | 4 | 5 |
| 5 | 3 | 3 |
| 6 | 2 | 2 |
| 7 | 1 | 1 |
| 8 | 1 | 1 |
| 9 | 0.5 | 0.6 |
| 10 | <0.4 | 0.4 |
| 11 | | <0.3 |
| 12 | | <0.3 |

The water-soluble soaps employed in the combars in accordance with the embodiment are sodium or potassium salts of natural or synthetic aliphatic (alkanoic or alkenoic) acids having a carbon chain length of about 8 to 20 carbon atoms. Examples of triglyceride sources providing soaps with carbon chain lengths in this range include coconut oil, palm kernel oil, babassu oil, ouricuri oil, tallow, palm oil, rice bran oil, groundnut oil and rapeseed oil. Preferred soap mixtures are prepared from coconut oil and tallow and comprise about 40% to 90% by weight of tallow fatty acids and about 10% to 60% by weight of coconut oil fatty acids. Such mixtures contain more than 90 wt % of fatty acids having carbon chain lengths in the $C_{12}$ to $C_{18}$ range. The preferred mixtures contain some unsaturated soaps, but excessive saturation is typically avoided.

The soaps used in the combars of the invention may be made by the classic kettle boiling process or fatty acid neutralization process or by more continuous soap manufacturing processes. These processes typically produce a neat soap containing from about 65 to 70 wt % of sodium soap, up to about 1.5 wt. % of glycerine, up to about 1 wt. % of salt, e.g., sodium chloride, and the balance water. Usually, neat soap is employed in the combars of the invention. Neat soap required in the formulas given below also can be made by mixing soap chips containing 14–20 wt. % of moisture and the necessary amount of water.

Eight examples of combar compositions in accordance with the second preferred embodiment were prepared using the following formulations:

EXAMPLE I

| Component | % (by weight) |
|---|---|
| Sodium Tallowate | 42.40 |
| Sodium Cocoate | 28.26 |
| NEGS-23 | 8.00 |
| Coco fatty acid | 3.50 |
| Stearic Acid | 3.50 |
| EDTA | 0.03 |
| Di-Tertiary Butyl-p-Cresol | 0.02 |
| Sodium Chloride | 1.20 |
| Glycerin | 1.55 |
| Free Oil | 1.54 |
| Titanium Dioxide | 0.50 |
| Fragrance | 1.50 |
| Moisture | 8.00 |

EXAMPLE II

| Component | % (by weight) |
|---|---|
| Sodium Tallowate | 37.49 |
| Sodium Cocoate | 25.00 |
| NEGS-23 | 15.00 |
| Coco fatty acid | 3.50 |
| Stearic Acid | 3.50 |
| EDTA | 0.03 |
| Di-Tertiary Butyl-p-Cresol | 0.02 |
| Sodium Chloride | 1.20 |
| Glycerin | 1.37 |
| Free Oil | 2.89 |
| Titanium Dioxide | 0.50 |
| Fragrance | 1.50 |
| Moisture | 8.00 |

EXAMPLE III

| Component | % (by weight) |
|---|---|
| Sodium Tallowate | 42.53 |
| Sodium Cocoate | 28.32 |
| NEGS-45 | 8.00 |
| Coco fatty acid | 3.50 |
| Stearic Acid | 3.50 |
| EDTA | 0.03 |
| Di-Tertiary Butyl-p-Cresol | 0.02 |
| Sodium Chloride | 1.20 |
| Glycerin | 1.55 |
| Free Oil | 1.35 |
| Titanium Dioxide | 0.50 |
| Fragrance | 1.50 |
| Moisture | 8.00 |

EXAMPLE IV

| Component | % (by weight) |
|---|---|
| Sodium Tallowate | 37.73 |
| Sodium Cocoate | 25.16 |
| NEGS-45 | 15.00 |
| Coco fatty acid | 3.50 |
| Stearic Acid | 3.50 |
| EDTA | 0.03 |
| Di-Tertiary Butyl-p-Cresol | 0.02 |
| Sodium Chloride | 1.20 |
| Glycerin | 1.38 |
| Free Oil | 2.53 |
| Titanium Dioxide | 0.50 |
| Fragrance | 1.50 |
| Moisture | 7.95 |

EXAMPLE V

| Component | % (by weight) |
|---|---|
| Sodium Tallowate | 49.60 |
| Sodium Cocoate | 21.25 |
| NEGS-45 | 8.00 |
| Coco fatty acid | 3.50 |
| Stearic Acid | 3.50 |
| EDTA | 0.03 |
| Di-Tertiary Butyl-p-Cresol | 0.02 |
| Sodium Chloride | 1.20 |
| Glycerin | 1.55 |
| Free Oil | 1.35 |
| Titanium Dioxide | 0.50 |
| Fragrance | 1.50 |
| Moisture | 8.00 |

EXAMPLE VI

| Component | % (by weight) |
|---|---|
| Sodium Tallowate | 60.22 |
| Sodium Cocoate | 10.63 |
| NEGS-45 | 8.00 |
| Coco fatty acid | 3.50 |
| Stearic Acid | 3.50 |
| EDTA | 0.03 |
| Di-Tertiary Butyl-p-Cresol | 0.02 |
| Sodium Chloride | 1.20 |
| Glycerin | 1.55 |
| Free Oil | 1.35 |
| Titanium Dioxide | 0.50 |
| Fragrance | 1.50 |
| Moisture | 8.00 |

EXAMPLE VII

| Component | % (by weight) |
|---|---|
| Sodium Tallowate | 38.43 |
| Sodium Cocoate | 25.62 |
| NEGS-45 | 7.00 |
| Sodium Cocoyl Isethionate | 8.00 |
| Coco fatty acid | 3.50 |
| Stearic Acid | 3.50 |
| EDTA | 0.03 |
| Di-Tertiary Butyl-p-Cresol | 0.02 |
| Sodium Chloride | 1.20 |
| Glycerin | 1.40 |
| Free Oil | 1.18 |
| Sodium Isethionate | 0.54 |
| Titanium Dioxide | 0.50 |
| Fragrance | 1.50 |
| Moisture | 7.58 |

EXAMPLE VIII

| Component | % (by weight) |
|---|---|
| Sodium Tallowate | 46.05 |
| Sodium Cocoate | 30.70 |
| NEGS-45 | 2.00 |
| Coco fatty acid | 3.50 |
| Stearic Acid | 3.50 |
| EDTA | 0.03 |
| Di-Tertiary Butyl-p-Cresol | 0.02 |
| Sodium Chloride | 1.20 |
| Glycerin | 1.69 |
| Free Oil | 0.31 |
| Titanium Dioxide | 0.50 |
| Fragrance | 1.50 |
| Moisture | 9.00 |

The combar in accordance with the second preferred embodiment of the invention, as shown by Examples I–VIII, is directed to the use of sodium salt of alcohol ethoxy glyceryl sulfonate in conjunction with a tallowate-cocoate fatty acid soap. Through the use of this particular anionic surfactant, there is produced a very mild soap composition which has very good lathering characteristics. This mildness is not exhibited by soap compositions which contain the same tallowate-cocoate formulation but which utilize different surfactants.

The anionic surfactants which exhibit this high degree of mildness with tallowate-cocoate soaps preferably are sodium salts of alcohol ethoxy glyceryl sulfonate wherein the radical is an alkyl group of 12 to 15 carbon atoms.

In accordance with a third preferred embodiment, a syndet bar composition includes anionic surfactants in addition to the sodium salt of alcohol ethoxy glyceryl sulfonate. Three examples were prepared using the following formulations:

EXAMPLE IX

| Component | % (by weight) |
|---|---|
| Sodium Tallowate Monoglyceride Sulfate | 11.32 |
| Sodium Cocoate Monoglyceride Sulfate | 33.96 |
| NEGS-45 | 9.44 |
| Sodium Tallowate | 6.43 |
| Sodium Cocoate | 1.13 |
| Stearic Acid | 20.76 |
| Di-Tertiary Butyl-p-Cresol | 0.02 |
| EDTA | 0.02 |
| Titanium Dioxide | 0.50 |
| Fragrance | 1.50 |
| Sodium Sulfate | 4.53 |
| Free Oil | 8.27 |
| Moisture | 2.12 |

EXAMPLE X

| Component | % (by weight) |
|---|---|
| Sodium Cocoyl Isethionate | 51.00 |
| NEGS-45 | 9.42 |
| Sodium Tallowate | 6.48 |
| Sodium Cocoate | 1.14 |
| Stearic Acid | 18.06 |
| Coco fatty acid | 5.09 |
| Di-Tertiary Butyl-p-Cresol | 0.02 |
| EDTA | 0.02 |
| Titanium Dioxide | 0.50 |
| Fragrance | 1.50 |
| Free Oil | 1.59 |
| Sodium Isethionate | 1.49 |
| Moisture | 3.69 |

EXAMPLE XI

| Component | % (by weight) |
|---|---|
| Sodium Cocoyl Isethionate | 51.76 |
| NEGS-23 | 9.69 |
| Sodium Tallowate | 6.88 |
| Sodium Cocoate | 1.21 |
| Stearic Acid | 16.23 |
| Coco fatty acid | 5.41 |
| Di-Tertiary Butyl-p-Cresol | 0.02 |
| EDTA | 0.02 |
| Titanium Dioxide | 0.50 |
| Fragrance | 1.50 |
| Free Oil | 1.96 |
| Sodium Isethionate | 1.51 |

| Component | % (by weight) |
|---|---|
| Moisture | 3.31 |

The ratio of saponified tallowate fatty acid to saponified cocoate fatty acid in the fatty acid soap component can range from about 10 weight % to about 90 weight % saponified tallowate fatty acid and from about 90 weight % to 10 weight % of saponified cocoate fatty acid. However, preferred compositions are those which contain from about 40% to about 90% saponified tallowate fatty acid and from about 10% to about 60% saponified cocoate fatty acid.

The above-described combars and syndets can be produced using any one of the conventional soapmaking techniques.

The in vitro collagen swelling assay was used to determine the mildness of various raw materials and various detergent bar formulas. The collagen film is placed in a 1% solution of detergent bar formula, which was labelled with radioactive tritiated water. The solution containing collagen film was incubated at 50° C. for 24 hours. After rinsing, the uptake of tritiated water by the collagen film was determined by counting. The swelling of the collagen film is defined as microliters of water uptake per milligram collagen ($\mu$l/mg). The relationship between irritancy, particularly erythema, and collagen swelling has been established (J. C. Blake-Hoskins, D. Scala, L. D. Rhein and C. R. Robbins, *J. Soc. Cosmet. Chem.*, 37, 199, 1986): the higher the water uptake, the greater the irritation potential.

The results of the collagen swelling tests for the raw materials and for the various combar formulations are respectively summarized in Tables 1 and 2. These results indicate that low level replacements by sodium ethoxylated alcohol ($C_{12}$–$C_{13}$) glyceryl sulfonate (NEGS-23), sodium ethoxylated alcohol ($C_{14}$–$C_{15}$) glyceryl sulfonate (NEGS-45) and sodium cocoyl isethionate (SCI) can significantly reduce the irritancy of soap, e.g., tallowate-cocoate soap. Replacements of soap by NEGS-23 and NEGS-45 show greater mildness benefits than replacement by SCI, which is used in a prior art combar as a mild surfactant at an 8% level.

TABLE 1

| Sample (1% solution) | Collagen Swelling ($\mu$l water/mg film) |
|---|---|
| Sodium Cocoyl Isethionate (SCI) | 6.85 ± 0.10 |
| Sodium Cocomonoglyceride Sulfate (CMGS) | 6.90 ± 0.14 |
| Sodium Alcohol ($C_{12}$–$C_{13}$) Glyceryl Sulfonate (AGES-23) | 6.53 ± 0.26 |
| Sodium Alcohol ($C_{14}$–$C_{15}$) Glyceryl Sulfonate (AGES-45) | 4.81 ± 0.12 |
| Sodium Alcohol ($C_{12}$–$C_{13}$) Ethoxy Glyceryl Sulfonate (NEGS-23) | 5.91 ± 0.30 |
| Sodium Alcohol ($C_{14}$–$C_{15}$) Ethoxy Glyceryl Sulfonate (NEGS-45) | 3.85 ± 0.22 |

TABLE 2

| Sample (1% solution) | Collagen Swelling ($\mu$l water/mg film) |
|---|---|
| 8% NEGS-23/Soap* Combar (Example I) | 9.37 ± 0.28 |
| 8% NEGS-45/Soap* Combar (Example III) | 9.98 ± 0.16 |
| 15% NEGS-45/Soap* Combar (Example IV) | 8.82 ± 0.18 |
| 8% SCI/Soap* Combar | 10.68 ± 0.27 |
| 22% SCI/Soap Combar | 8.92 ± 0.43 |
| Soap*/8% Water | 12.58 ± 0.24 |
| Soap*/15% Water | 12.69 ± 0.23 |
| Soap* | 12.96 ± 0.48 |

*The soap used included sodium tallowate/sodium cocoate in a ratio of 60:40, 3.5% coco fatty acid and 3.5% stearic acid.

The soap irritancy may be further reduced by increasing the level of sodium ethoxylated alcohol glyceryl sulfonate. It is clear that replacement of water in tallowate-cocoate soap has no mildness benefits. This implies that the mildness benefit is not due to dilution by the surfactants.

Skin tightness and dryness are caused by soap binding to skin after washing and rinsing. The quantitative analysis of the binding of radioactive soap to wool fabric was used as an in vitro assay to evaluate the level of soap binding to skin.

Radioactive palmitic acid (C-14) was used as a probe of soap binding to wool fabric. Accurately weighted wool fabric was placed in 10 ml of 5% soap solution at 300 ppm hardness, which is labelled with radioactive palmitic acid. After 24 hours incubation at 50° C., the wool fabric was filtered and placed in 10 ml of 300 ppm hardness water and incubated at 50° C. for another 24 hours. After filtration, the wool fabric was digested and counted for radioactivity to determine the amount of bound soap, in micromoles of soap residue per gram of wool fabric ($\mu$mol/g).

The experimental data for soap residue left on wool swatches after rinsing are shown in Table 3. Soap residue is significantly reduced by adding NEGS-23, NEGS-45 and SCI to tallowate-cocoate soap.

TABLE 3

| Sample* (5% solution) | Palmitic Soap Residue ($\mu$mol/g wool) |
|---|---|
| 8% NEGS-23/92% Soap | 29 ± 1 |
| 15% NEGS-23/85% Soap | 24 ± 2 |
| 8% NEGS-45/92% Soap | 29 ± 1 |
| 15% NEGS-45/85% Soap | 21 ± 1 |
| 8% SCI/92% Soap | 33 ± 1 |
| 15% SCI/85% Soap | 27 ± 1 |
| 8% Water/92% Soap | 42 ± 4 |
| 15% Water/85% Soap | 43 ± 2 |
| 100% Soap | 44 ± 1 |

*The soap used included sodium tallowate/sodium cocoate in a ratio of 60:40, 3.5% coco fatty acid and 3.5% stearic acid.

The results show that the soap residue left on wool swatches decreases with increasing replacement of soap by NEGS-23 and NEGS-45. Obviously NEGS has a greater ability to reduce soap residue than SCI. Eight percent replacement by NEGS reduces the soap residue to the same value as 15% replacement by SCI. Replacements of soap by 8% and 15% of water did not improve the rinsability. This suggests that the interactions between surfactant and soap reduced the soap binding to wool fabric.

The results of collagen swelling tests for various syndet bar formulations are summarized in Table 4. Clinical observations and instrumental measurements of irritation and dryness were made for the three syndet bars in accordance with the invention (see Examples IX, X and XI above) relative, the reference syndet bars (A and B) described in Table 4 and other syndet bars in a modified soap chamber test. The syndet bar of Example IX (comprising tallow/coco monoglyceride sulfate and NEGS-45) induced the least irritation; reference syndet bar A (comprising SCI) and a third reference syndet bar C (comprising SCI and AGES-45) induced the most irritation. Other syndet bars, including those of Example X (comprising SCI and NEGS-23), Example XI

TABLE 4

| Sample (1% solution) | Collagen Swelling (μl water/mg film) |
|---|---|
| Example IX | 4.67 ± 0.13 |
| Example X | 5.12 ± 0.06 |
| Example XI | 5.72 ± 0.18 |
| Reference Syndet Bar A* | 6.01 ± 0.21 |
| Reference Syndet Bar B** | 5.24 ± 0.05 |

*Composition: 57.15% SCI, 18.83% stearic acid, 6.76% sodium tallowate, 5.31% coco fatty acid, 1.69% sodium isethionate, 1.19% sodium cocoate and other ingredients.
**Composition: 48.3% AGES, 15.9% fatty acid, 12.5% sodium sarcosinate, 7.8% soap and other ingredients.

(comprising SCI and NEGS-45) and reference syndet bar B (comprising AGES), were intermediate in mildness with some products being milder as measured by one technique but not another.

This ranking is based on both visual assessments and instrumental observations after 24 and 48 hours of patching. The products that were ranked least in irritation had consistently among the lowest erythema, change in skin redness (Minolta a* value) and change in transepidermal water loss. Conversely, the products ranked the highest in irritation induced the most changes in these parameters. The products in the middle produced moderate amounts of irritation. Occasionally, these products may have been extremely mild or irritating but for the most part were always ranked in the middle.

The foregoing test results show that the presence of low levels of sodium ethoxylated alcohol glyceryl sulfonate in a detergent bar formula is highly beneficial to clinical mildness and rinsability of soap. It has been found that adding low levels, that is, from 1 to 60 wt. %, of sodium ethoxylated alcohol glyceryl sulfonate to tallowate-cocoate soap will significantly reduce the irritancy of soap with respect to erythema, tightness and dryness.

In the alternative, beneficial results are obtained by replacement of soap with mixtures of NEGS and one or more of the following: SCI, disodium alkylamido MEA sulfosuccinates, sodium alkyl sarcosinate, sodium tallow monoglyceride sulfate, sodium cocoyl monoglyceride sulfate.

NEGS also has efficacy in personal cleansing products other than soap. In accordance with a fourth preferred embodiment, milder shampoo compositions are obtained by the addition of NEGS. Such compositions are especially useful in baby shampoos. Six examples of shampoo compositions formulated by the inventors in accordance with the invention are given below:

EXAMPLE XII

| Component | % (by weight) |
|---|---|
| Alcohol Ethoxy Glyceryl Sulfonate | 10.00 |
| Cocoamide Diethanolamide or Monoethanolamide | 4.00 |
| Deionized Water | Q.S. |
| Sodium or Ammonium Alpha Olefin Sulfonate | 5.00 |
| Perfume | 0.50 |
| Germaben II | 0.50 |
| Colors | Q.S. |
| Sodium Chloride | 0.60 |
| Ammonium Phosphate (Monobasic) | 0.25 |

EXAMPLE XIII

| Component | % (by weight) |
|---|---|
| Alcohol Ethoxy Glyceryl Sulfonate | 13.00 |
| Cocoamide Diethanolamide or Monoethanolamide | 4.00 |
| Deionized Water | Q.S. |
| Perfume | 0.50 |
| Germaben II | 0.50 |
| Colors | Q.S. |
| Sodium Chloride | 0.60 |
| Ammonium Phosphate (Monobasic) | 0.25 |

EXAMPLE XIV

| Component | % (by weight) |
|---|---|
| Alcohol Ethoxy Glyceryl Sulfonate | 15.00 |
| Deionized Water | Q.S. |
| Hydroxy Ethyl Cellulose, Methocel or Xanthum Gum | 0.50 |
| Perfume | 0.50 |
| Germaben II | 0.50 |
| Colors | Q.S. |
| Sodium Chloride | 0.60 |
| Ammonium Phosphate (Monobasic) | 0.10 |

EXAMPLE XV

| Component | % (by weight) |
|---|---|
| Alcohol Ethoxy Glyceryl Sulfonate | 10.00 |
| Cocoamide Diethanolamide or Monoethanolamide | 4.00 |
| Deionized Water | Q.S. |
| Ammonium Lauryl Sulfate | 5.00 |
| Cocoamidopropyl Betaine | 3.00 |
| Perfume | 0.50 |
| Germaben II | 0.50 |
| Colors | Q.S. |
| Sodium Chloride | 0.60 |
| Ammonium Phosphate (Monobasic) | 0.25 |

EXAMPLE XVI

| Component | % (by weight) |
|---|---|
| Alcohol Ethoxy Glyceryl Sulfonate | 10.00 |
| Cocoamide Diethanolamide or Monoethanolamide | 4.00 |
| Deionized Water | Q.S. |
| Ammonium Lauryl Sulfate | 5.00 |
| Cocoamidopropyl Betaine | 3.00 |
| Perfume | 0.50 |
| Germaben II | 0.50 |
| Colors | Q.S. |
| Sodium Chloride | 0.60 |
| Ammonium Phosphate (Monobasic) | 0.25 |

EXAMPLE XVII

| Component | % (by weight) |
|---|---|
| Alcohol Ethoxy Glyceryl Sulfonate | 10.00 |

| Component | % (by weight) |
|---|---|
| Citric Acid | 0.05 |
| Cocoamidopropyl Betaine (L7) | 4.00 |
| Hydroxy Ethyl Cellulose (250 HHR) | 0.30 |
| Tween 40 | 3.00 |
| Color | 0.01 |
| Germaben II | 0.50 |
| Glycerin | 1.50 |
| Ammonium Phosphate | 0.01 |
| Deionized Water | Q.S. |

The baby shampoo formulation of Example XVII is clear and has a viscosity of 2500-3500 cps and pH 6.8-7.2.

In the formulations of Examples XII through XVII, the amides and betaine serve as foam and viscosity boosters/stabilizers. The salts and gums serve to build viscosity/lather.

The secondary anionic surfactants to be included in shampoo compositions in accordance with the third preferred embodiment are not limited to those identified in Example XII through XVII. Any alcohol ether sulfate of carbon chain length $C_{10}$ to $C_{16}$, preferably $C_{12}$ to $C_{14}$, with an ethoxylation range of 0 to 7EO, preferably 2-4EO and preferably narrow range ethoxylates, could be used in conjunction with sodium alcohol ethoxy glyceryl sulfonate.

Such combinations provide a shampoo system which is high-foaming and an effective lipid soil remover, yet is mild to skin and hair. For example, lipid soil removal for SLES-3EO (narrow range ethoxylate) was 85±2%; for SLES-3EO/NEGS-23 in a ratio of 12:3 was 83±2%; and for SLES-3EO/NEGS-23 in a ratio of 10:5 was 85±2%. Any value above 80% sebum removal represents extremely high activity.

In accordance with a fifth preferred embodiment, milder liquid soap and bubble bath compositions are obtained by the addition of sodium alcohol ethoxy glyceryl sulfonate. The details of five examples of such compositions formulated by the inventors in accordance with the invention are given below:

EXAMPLE XVIII

| Component | % (by weight) |
|---|---|
| Alcohol Ethoxy Glyceryl Sulfonate | 10.00 |
| Deionized Water | Q.S. |
| Sodium or Ammonium Alpha Olefin Sulfonate | 5.00 |
| Cocoamidopropyl Betaine | 2.50 |
| Hydroxy Ethyl Cellulose, Methocel or Xanthum Gum | 0.20 |
| Perfume | 0.50 |
| Germaben II | 0.50 |
| Colors | Q.S. |
| Ammonium Phosphate (Monobasic) | 0.10 |

EXAMPLE XIX

| Component | % (by weight) |
|---|---|
| Alcohol Ethoxy Glyceryl Sulfonate | 10.00 |
| Cocoamide Diethanolamide (DEA) or Monoethanolamide (MEA) | 4.00 |
| Deionized Water | Q.S. |
| Sodium, Ammonium or Triethanolamide (TEA) Lauryl Sulfate | 2.00 |
| Sodium or Ammonium Alpha Olefin Sulfonate | 2.00 |
| Cocoamidopropyl Betaine | 2.00 |
| Perfume | 0.50 |
| Germaben II | 0.50 |
| Colors | Q.S. |
| Sodium Chloride | 0.50 |
| Ammonium Phosphate (Monobasic) | 0.25 |

EXAMPLE XX

| Component | % (by weight) |
|---|---|
| Alcohol Ethoxy Glyceryl Sulfonate | 15.00 |
| Cocoamide DEA or MEA | 2.00 |
| Deionized Water | Q.S. |
| Sodium or Ammonium Alpha Olefin Sulfonate | 2.00 |
| Cocoamidopropyl Betaine | 2.00 |
| Hydroxy Ethyl Cellulose, Methocel or Xanthum Gum | 0.20 |
| Polyquaternium (e.g., Merquat 550) | 0.20 |
| Perfume | 0.50 |
| Germaben II | 0.50 |
| Colors | Q.S. |
| Sodium Chloride | 0.50 |
| Ammonium Phosphate (Monobasic) | 0.35 |

EXAMPLE XXI

| Component | % (by weight) |
|---|---|
| Alcohol Ethoxy Glyceryl Sulfonate | 5.00 |
| Cocoamide DEA or MEA | 3.00 |
| Deionized Water | Q.S. |
| Sodium or Ammonium or TEA Lauryl Sulfate | 5.00 |
| Sodium or Ammoinium Alpha Olefin Sulfonate | 5.00 |
| Cocoamidopropyl Betaine | 2.50 |
| Hydroxy Ethyl Cellulose, Methocel or Xanthum Gum | 0.25 |
| Perfume | 0.50 |
| Germaben II | 0.50 |
| Colors | Q.S. |
| Sodium Chloride | 0.50 |
| Ammonium Phosphate (Monobasic) | 0.20 |

EXAMPLE XXII

| Component | % (by weight) |
|---|---|
| Alcohol Ethoxy Glyceryl Sulfonate | 20.00 |
| Cocoamide DEA or MEA | 3.00 |
| Deionized Water | Q.S. |
| Perfume | 0.50 |
| Germaben II | 0.50 |
| Colors | Q.S. |
| Ammonium Phosphate (Monobasic) | 0.25 |

In accordance with a sixth preferred embodiment, milder shower gel compositions are obtained by the addition of sodium alcohol ethoxy glyceryl sulfonate. The details of three examples of such compositions formulated by the inventors in accordance with the invention are given below:

EXAMPLE XXIII

| Component | % (by weight) |
|---|---|
| Alcohol Ethoxy Glyceryl Sulfonate | 10.00 |
| Cocoamide Diethanolamide or | 5.00 |

-continued

| Component | % (by weight) |
|---|---|
| Monoethanolamide | |
| Deionized Water | Q.S. |
| Cocoamidopropyl Betaine | 2.50 |
| Hydroxy Ethyl Cellulose, Methocel or Xanthum Gum | 0.25 |
| Perfume | 0.50 |
| Germaben II | 0.50 |
| Colors | Q.S. |
| Sodium Chloride | 0.50 |
| Ammonium Phosphate (Monobasic) | 0.30 |

EXAMPLE XXIV

| Component | % (by weight) |
|---|---|
| Alcohol Ethoxy Glyceryl Sulfonate | 15.00 |
| Cocoamide Diethanolamide or Monoethanolamide | 4.00 |
| Deionized Water | Q.S. |
| Sodium, Ammonium or Triethanolamide Lauryl Sulfate | 5.00 |
| Cocoamidopropyl Betaine | 2.50 |
| Perfume | 0.50 |
| Germaben II | 0.50 |
| Colors | Q.S. |
| Sodium Chloride | 0.20 |
| Ammonium Phosphate (Monobasic) | 0.20 |

EXAMPLE XXV

| Component | % (by weight) |
|---|---|
| Alcohol Ethoxy Glyceryl Sulfonate | 20.00 |
| Deionized Water | Q.S. |
| Cocoamidopropyl Betaine | 2.50 |
| Polyquaternium (e.g., Merquat 550) | 0.25 |
| Perfume | 0.50 |
| Germaben II | 0.50 |
| Colors | Q.S. |
| Ammonium Phosphate (Monobasic) | 0.10 |

Although specific compositions in accordance with the fourth, fifth and sixth embodiments have been formulated, it will be readily appreciated that the amounts of each components may be varied over wide ranges. For example, the surfactants of the shampoo compositions in accordance with the fourth preferred embodiment may be varied over the following ranges:

TABLE 5

| Component | Range (wt. %) |
|---|---|
| Alcohol Ethoxy Glyceryl Sulfonate | 2-25 |
| Cocamide DEA or MEA | 0-10 |
| Sodium, Ammonium or TEA Lauryl Sulfate | 0-20 |
| Sodium or Ammonium Alpha Olefin Sulfonate | 0-20 |
| Cocoamidopropyl Betaine | 0-20 |
| Polysorbates (Tween 20, 40, 60, etc.) | 0-8 |

Similarly, the surfactants of the liquid soap or bubble bath compositions in accordance with the fifth embodiment may be varied over the following ranges:

TABLE 6

| Component | Range (wt. %) |
|---|---|
| Alcohol Ethoxy Glyceryl Sulfonate | 2-25 |
| Cocamide DEA or MEA | 0-10 |
| Sodium, Ammonium or TEA Lauryl Sulfate | 0-20 |
| Sodium or Ammonium Alpha Olefin Sulfonate | 0-20 |
| Cocoamidopropyl Betaine | 0-20 |
| Polysorbates (Tween 20, 40, 60, etc.) | 0-8 |

Finally, the surfactants of the shower gel compositions in accordance with the sixth preferred embodiment may be varied over the following ranges:

TABLE 7

| Component | Range (wt. %) |
|---|---|
| Alcohol Ethoxy Glyceryl Sulfonate | 2-25 |
| Cocamide DEA or MEA | 0-10 |
| Sodium, Ammonium or TEA Lauryl Sulfate | 0-20 |
| Cocoamidopropyl Betaine | 0-20 |
| Polysorbates (Tween 20, 40, 60, etc.) | 0-8 |

The preferred embodiments have been described in detail hereinabove for the purpose of illustration only. It will be apparent to a practitioner of ordinary skill in the art of personal hygiene products that various modifications could be made to the above-described formulas without departing from the spirit and scope of the invention as defined in the claims set forth hereinafter. For example, the degree of ethoxylation of the sodium salt of alcohol ethoxy glyceryl sulfonate could be increased to obtain milder products. Also the carbon chain length of the alcohol ethoxy glyceryl sulfonate radical can be varied.

Furthermore, in addition to the primary alcohol ethoxy glyceryl sulfonate surfactant, the liquid compositions of the fourth, fifth and sixth preferred embodiments may also include up to 20 wt. %, preferably 2–10 wt. %, of a water-soluble, additional anionic surfactant for the purpose of improving the detergency and foaming properties of the primary surfactant. Generally, the additional surfactant improves both the foam stability and foam volume of the primary surfactant. However, the additional surfactant has the disadvantage of being more irritating than the primary surfactant which is characterized by its mildness. Thus, the concentration of the additional surfactant is related to the concentration of the primary surfactant, and the weight ratio of primary surfactant to additional surfactant usually range from about 1:1 to about 20:1, preferably 1.5:1 to 6:1.

Satisfactory additional surfactants are water-soluble, non-soap, anionic surfactants having in their molecular structure a $C_7$–$C_{22}$ alkyl, alkenyl or acyl group and a sulfonate, sulfate or carboxylate group. Such surfactants are employed in the form of water-soluble salts and the salt-forming cation usually is selected from the group consisting of sodium, potassium, ammonium, and mono-, di- or tri-$C_2$–$C_3$ alkanolammonium, with the sodium and ammonium cations again being preferred.

The suitable supplementary anionic surfactants include the following:

1. The $C_8$–$C_{18}$ alkyl sulfates which are usually obtained by sulfating $C_8$–$C_{18}$ alkanols obtained by reducing the glycerides of tallow or coconut oil. Preferred alkyl sulfates contain 10 to 16 carbon atoms in the alkyl group.

2. The $C_9$–$C_{15}$ alkylbenzene sulfonates wherein the alkyl group is a straight chain or a branched chain, with the straight chain being preferred for its improved biodegradability.

3. The $C_8$–$C_{22}$ olefin sulfonates which may be obtained by sulfating the appropriate olefin. Preferred olefin sulfonates contain 14 to 16 carbon atoms in the alkyl group and are obtained by sulfonating and olefin.

4. The $C_8$–$C_{18}$ alkyl ether ethylenoxy sulfates of the formula:

$$R(OC_2H)_nOSO_3M$$

wherein n is 1 to 4. Preferred alkyl ether ethylenoxy sulfates contain 12 to 16 carbon atoms in the alkyl group and contain two to three ethylene oxide groups per mole of alkanol.

5. The $C_{10}$–$C_{20}$ paraffin sulfonates obtained, for example, by reacting an $\mu$-olefin with bisulfate. Preferred alkane sulfates contain 13 to 17 carbon atoms in the alkyl group.

6. The $C_6$–$C_{12}$ phenyl ether polyethylenoxy sulfates containing from 2 to 6 moles of ethylene oxide may also be used. These surfactants can be prepared by reacting an alkyl phenol with 2 to 6 moles of ethylene oxide and sulfating and neutralizing the resultant ethoxylated alkylphenol. Preferred surfactants in this group have 8 to 12 carbon atoms in the alkyl group and contain about 4 ethylene oxide groups in the molecule.

7. The $C_8$–$C_{18}$ alkyl sulfoacetates corresponding to the formula:

$$ROOCCH_2SO_3M$$

wherein R is a $C_8$–$C_{18}$ alkyl which may be prepared by esterifying an alkanol with chloroacetate acid or chloroacetyl chloride and then reacting the chloroester with a sodium or potassium bisulfate. Preferred sulfoacetates contain 12 to 16 carbon atoms in the alkyl group.

8. The N-mono-$C_8$–$C_{22}$ alkyl (includes alkyl groups interrupted by an ether or amido group) sulfosuccinates prepared by reacting, for example, either one mole of corresponding to $C_8$–$C_{18}$ alkanol or a $C_8$–$C_{18}$ alkoxy $C_2$–$C_3$ alkanol or a $C_8$–$C_{18}$ alkanamido $C_2$–$C_3$ alkanol with maleic acid and reacting the resultant product with an alkali metal bisulfite to form an N-mono-$C_8$–$C_{22}$ alkyl sulfosuccinate. It should be recognized that the alkyl group of product made from the N-acyl alkanolamine will contain an amido intermediate linkage. Similarly, the alkyl group may be interrupted by an ether linkage or ester linkage if an alkyl ether ethanol or an alkyl ester of ethylene glycol is reacted with maleic acid. Preferred sulfosuccinates are disodium N-mono-$C_8$–$C_{18}$ acylisopropanolaluminosulfosuccinate, disodium lauryl sulfosuccinate and N-monooleyliso-propanolaluminosulfosuccinate.

9. The N-$C_8$–$C_{18}$ acyl sarcosines which may be produced by neutralizing the reaction product of $C_8$–$C_{18}$ alkanoic acid with N-methyl glycine. Preferred sarcosinates contain 12 to 14 carbon atoms in an acyl group obtained by reduction of coconut oil.

10. The N-$C_8$–$C_{18}$ acyl taurines which may be produced by neutralizing the reaction product of $C_8$–$C_{18}$ alkanoic acid with aminoethylsulfonic acid. Again, preferred taurates contain 12 to 14 carbon atoms in an acyl group obtained by reduction of coconut oil.

11. The O—$C_8$–$C_{18}$ acyl isethionates which may be produced by neutralizing the reaction product of $C_8$–$C_{18}$ alkanoic acid with 2-hydroxyethanesulfonic acid. Similar to the sarcosines and taurines, the preferred isethionates contain 12 to 14 carbon atoms in an acyl group obtained by reduction of coconut oil.

As indicated above, the proportion of the additional anionic surfactant must be controlled if the final composition is to be mild to the skin because the additional anionic surfactants are more irritating to the skin than the principal alcohol ethoxy glyceryl sulfonate surfactant. Although the additional surfactants are included to improve the foaming and detergency properties of the inventive liquid compositions, it should be understood that the concentration present will be maintained at the minimum level consistent with the desired performance characteristics in order to preserve the mildness of the final product. Thus, the proportions of the individual additional anionic surfactants are variable and will be based upon an appropriate integration of foaming, cleaning and mildness properties of the individual additional surfactants with the primary alcohol ethoxy glyceryl sulfonate surfactant.

Furthermore, although the preferred zwitterionic surfactant used in the liquid compositions of the fourth through sixth preferred embodiments of the invention is cocoamidopropyl betaine, other zwitterionic surfactants can be used. The zwitterionic surfactant used corresponds to the formula:

$$\begin{array}{c} R_1 \\ | \\ R-N^+-R_2XOO- \\ | \\ R_1 \end{array}$$

wherein R is $C_8$–$C_{18}$ alkyl or $C_8$–$C_{18}$ alkanolamido $C_2$–$C_3$ alkyl, $R_1$ is $C_1$–$C_3$ alkyl, $R_2$ is $C_1$–$C_4$ alkylene or $C_1$–$C_4$ hydroxy alkylene, and X is C or S:O. When X is C, the surfactant is called betaine; when X is S:0, the surfactant is called a sultaine or sulfobetaine. These zwitterionic surfactants can be described broadly as derivatives of aliphatic quaternary ammonium or tertiary sulfonium compounds containing a $C_8$–$C_{18}$ aliphatic radical which may be straight chained or branch chained and containing an anionic group. Preferred betaine and suitaine surfactants are laurylmethylammonioacetate, myristyldimethylammonioacetate, $C_8$–$C_{18}$ alkanamidopropyl-dimethylammonioacetate, 1-(myristyldimethylammonio)propane-3-sulfonate and 1-(myristyldimethylammonio)-2-hydroxypropane-3-sulfonate.

In the inventive liquid compositions, the zwitterionic surfactant acts as both a foam builder and as a counter-irritant detergent. Generally, the proportion of zwitterionic surfactant in the liquid compositions will range from 0 to 20 wt. %, preferably 2 to 6 wt. %. Further, the proportion of zwitterionic surfactant will be integrated with the proportion of the supplementary anionic surfactant in view of its apparent counter-irritant effects and, desirably, the weight ratio of zwitterionic surfactant to supplementary anionic surfactant will be from 2:1 to 1:3. Additionally, the zwitterionic surfactant concentration will be coordinated with the alkanoic acid alkanolamide foam booster in order to achieve liquid compositions of optimum foam stability. Finally, although the preferred alkanoic acid alkanolamide used in the liquid compositions of the invention is cocoamide diethanolamide or monoethanol-amide, other $C_8$–$C_{18}$ alkanoic acid $C_2$–$C_3$ alkanolamides can be used. This component is widely recognized as a foam builder. Satisfactory alkanoic acid alkanolamides are lauric monoethanolamide, myristic monoethanolamide, lauric diethanolamide, myristic diethanolamide, lauric isopropanolamide, and coconut ($C_8$–$C_{18}$) monoethanolamide. Preferred alkanoic acid alkanolamides contain 12 to 14 carbon atoms in the fatty acyl group.

The proportions of the alkanoic acid alkanolamide and the zwitterionic surfactant are controlled in the range of 1:4 to 4:1, preferably 1:2 to 2:1, in order to provide optimum foam stability. Usually, the amount of alkanoic acid alkanolamide in the liquid composition will be up to 10 wt. %, preferably 2 to 6 wt. %.

As shown in prior examples the sodium salt of alcohol ethoxy glyceryl sulfonate (NEGS) in combination with a soap such as a standard tallowate-cocoate fatty acid soap produces a cleansing composition which is very mild and has good lathering characteristics. Such tallowate cocoate soap has a relatively complete distribution of fatty acids around the preferred $C_{12}$–$C_{18}$ range. It has been found that a "topped" cocoate fatty acid soap, that is a material wherein the lowest fatty acids ($C_6$–$C_{10}$) soap are reduced in number or removed completely, provides a cleansing composition which performs better than a composition having the normal full distribution tallowate and cocoate soap. Such topped cocoate cleansing compositions are commercially produced.

As shown by the tables below it has now been observed that even with this improved soap containing cleansing composition, the partial replacement of the "topped" soap with sodium salt of alcohol ethoxy glyceryl sulfonate brings about a surprisingly superior performing bar with respect to 1. mildness, see collagen swelling assay data below;
2. skin tightness and dryness related to soap binding, see quantitative analysis of the binding of radioactive soap to wool fabric data below; and
3. soap processing.

In each of these situations, it is noted that the NEGS performed better on a weight basis than another anionic surfactant, sodium cococyl isethionate.

The topped coco soap fraction used in the tested compositions had the following fatty acid distribution:

| Carbon Number | Wt % |
|---|---|
| 10 | 0.6 |
| 12 | 56.0 |
| 14 | 22.1 |
| 16 | 10.4 |
| 18 | 2.6 |
| 18:1[a] | 6.5 |
| 18:2[b] | 1.5 |

[a] One double bond in chain.
[b] Two double bonds in chain.

Average molecular weight of topped coco fatty acid was 221 and iodine value as measured by Wijs method was 8.

Combars were prepared by adding pre-weighed NEGS slurry to a calculated amount of topped coco neat soap in a steam jacketed kettle under constant agitation. A desired amount of superfatting acid in the molten form was also introduced into mixture. The homogeneous soap mixture was dried in an oven to reduce the moisture level to a range of 10 to 13%. Soap chips were then processed into bars using conventional roll-mill, extruder and press according to the formulations shown in Table 8 for combars containing 0, 15, 20 and 25% NEGS-45. It was also observed that the presence of NEGS improved the processability of topped coco soap.

TABLE 8

Combar formulations containing topped coco soap and 0%, 10%, 15%, 20% and 25% of NEGS-45.

| Formulation Wt. % | Example | | | | |
|---|---|---|---|---|---|
| | 26 | 27 | 28 | 29 | 30 |
| Top Coco Soap | 77.72 | 67.35 | 62.18 | 57.14 | 51.82 |
| NEGS-45 | — | 10.00 | 15.00 | 20.00 | 25.00 |
| Free Oil[a] | — | 1.46 | 2.19 | 2.91 | 3.64 |
| Sodium Chloride | 1.23 | 1.07 | 0.98 | 0.87 | 0.82 |
| Fatty Acid | 7.00 | 6.07 | 5.60 | 5.03 | 4.07 |
| EDTA | 0.03 | 0.03 | 0.03 | 0.03 | 0.03 |
| BHT[b] | 0.02 | 0.02 | 0.02 | 0.02 | 0.02 |
| Water | 12.00 | 12.00 | 12.00 | 12.00 | 12.00 |
| Titanium Dioxide | 0.50 | 0.50 | 0.50 | 0.50 | 0.50 |
| Fragrance | 1.50 | 1.50 | 1.50 | 1.50 | 1.50 |

[a] non-surfactant organic compounds
[b] BHT is butylated hydroxy toluene.

The collagen swelling assay as described earlier in this patent application was used to assess the mildness of the detergent compositions. Below are the results:

TABLE 9

| Formula | Collagen Swelling (μl/mg) |
|---|---|
| Top Coco Soap | 14.36 +/− 0.87 |
| 15% NEGS-45 Top Coco Combar | 11.73 +/− 0.40 |
| 20% NEGS-45 Top Coco Combar | 10.87 +/− 0.79 |
| 25% NEGS-45 Top Coco Combar | 9.99 +/− 02.4 |
| 15% SCI Top Coco Combar | 14.18 +/− 0.14 |
| 20% SCI Top Coco Combar | 13.43 +/− 0.83 |
| 25% SCI Top Coco Combar | 12.36 +/− 0.87 |

The replacement of topped coco soap by either NEGS or SCI brings about a lower irritation level as measured by the assay. The NEGS performs better than SCI on a weight to weight basis.

The binding of radioactive soap to wool fabric assay as described earlier in this application was used to assess skin tightness and dryness related to soap binding. Below are the results:

TABLE 10

| Formula | Laurate Soap Residue Collagen Swelling (μmol/g wool) |
|---|---|
| Top Coco Soap | 69.4 +/− 3.4 |
| 15% NEGS-45 Top Coco Soap | 34.1 +/− 2.4 |
| 20% NEGS-45 Top Coco Soap | 30.2 +/− 1.1 |
| 25% NEGS-45 Top Coco Soap | 27.5 +/− 0.7 |
| 15% SCI Top Coco Soap | 50.4 +/− 1.7 |
| 20% SCI Top Coco Soap | 50.1 +/− 2.4 |
| 25% SCI Top Coco Soap | 45.4 +/− 5.0 |
| 15% Water Top Coco Soap | 68.0 +/− 2.6 |
| 20% Water Top Coco Soap | 70.2 +/− 2.4 |
| 25% Water Top Coco Soap | 72.4 +/− 4.0 |

The quantity of soap residue on wool swatches is reduced by adding NEGS and reducing topped coco soap. The NEGS performs better than SCI on a weight to weight basis.

Additionally, topped coco combars with various levels of NEGS (0, 10 and 15 wt %) were tested against Lever 2000, a potentially competitive product in a lather intensity trained panel setting. A group of nine male judges trained in Lather Profiling participated in the study. All sensory evaluations were conducted in a sequential monadic fashion. Replicate evaluations (3) were conducted for each product. Due to limitations in base availability, the Topped Coco with 0% NEGS was tested in a different shape from 10% NEGS, 15% NEGS, and Lever 2000. [It was included in the test as more of a guiding tool.] All bar pressing was performed in a Soap Pilot lab. The Standard (Irish Spring) was included in the test.

Using a standard washing procedure, the panelists evaluated each product on bar slip, bar softness, bar grit, bubble-size, quickness to lather, thick lather, amount of lather, rinsability of lather, and slip feel of wet skin. An Analysis of Variance procedure was performed on the monadic data.

The following statistically significant differences were noted.

All three of the Topped Coco bars (0%, 10%, and 15% NEGS) had lower bar slip, more lather, and had a thicker lather than Lever 2000. There were several other differences observed between the Topped Coco bars and Lever: Both the 10% and 15% NEGS had higher skin slip and larger bubbles than Lever 2000. The 10% NEGS also lathered quicker than Lever 2000.

There were few differences among the lather attributes among the 3 Topped Coco bars. The only difference that emerged was the 0% NEGS had significantly lower skin slip than both 10% and 15% NEGS. No differences were observed between 10% and 15% NEGS prototypes. In summary, addition of NEGS to topped coco soap, significantly improves mildness and rinsability, while maintaining the lather performance.

The surfactant of this invention can be formulated into a bar without any traditional soap being present as in accordance with the first preferred embodiment. Below is an example of this formulation.

EXAMPLE XXXI

| SCI | 51.70% |
|---|---|
| NEGS 45-1 | 10.00% |
| *Additive | 8.00% |
| Stearic Acid | 16.23% |
| Coco Fatty Acid | 5.41% |
| BHT | 0.02% |
| EDTA | 0.02% |
| Free Oil | 1.36% |
| Sodium Isethionate | 1.51% |
| Titanium Dioxide | 0.50% |
| Fragrance | 1.50% |
| Moisture | 3.69% |

*Additive - Tallow Alcohol; Corn Starch; Dry Flo (modified corn starch); Dermacryl 79 (Acrylates/t-Octylpropenamide copolymer); or their mixtures.

A cocoate bar with NEGS is exemplified below and is a preferred composition.

EXAMPLE XXXII

| Regular Coco Soap | 62.20% |
|---|---|
| NEGS 45-1 | 15.00% |
| Free Oil | 2.19% |
| Topped Coco Fatty Acid | 7.00% |
| Glycerine | 1.36% |
| Sodium Chloride | 1.20% |
| EDTA | 0.03% |
| BHT | 0.02% |
| Titanium Dioxide | 0.50% |
| Moisture | 9.00% |
| Fragrance | 1.50% |

Regular coco soap differs from topped coco soap in that it contains small amounts of C-6, C-8 and C-10 soaps, which are essentially absent in topped coco soap.

Throughout the specification, the personal cleansing attributes of the claimed compositions have been emphasized. Therefore the preferred physical forms of the compositions are those that are readily hand held and deliverable to the body in that form. For example, a solid delivery system is preferably hand held and therefore of a size and shape so as to be readily held in the hand, for example a bar. The liquid form of the compositions are preferably packaged in a container which fits readily into the hand, for example, pouring, squeezing or pumping purposes and is generally marketed and distributed in that manner. Examples of such packaged liquid compositions are a metal or plastic can with an orifice from which individual quantities of compositions can be poured, pumped or squeezed therefrom or in any other manner released therefrom by simple hand action.

We claim:

1. A personal cleansing composition comprising a salt of alcohol ethoxy glyceryl sulfonate and at least 1% of a further detergent surfactant.

2. The personal cleansing composition as defined in claim 1, wherein said salt is sodium.

3. The personal cleansing composition as defined in claim 1, wherein the surfactant is soap.

4. The personal cleansing composition as defined in claim 3, wherein said composition is in the form of a bar and the amount of said salt of alcohol ethoxy glyceryl sulfonate is in the range of 1 to 60 wt. %.

5. The personal cleansing composition as defined in claim 1, wherein said salt of alcohol ethoxy glyceryl sulfonate is the primary anionic surfactant wherein the surfactant is anionic surfactant.

6. The personal cleansing composition as defined in claim 5, wherein said anionic surfactant is alcohol ether sulfate.

7. The personal cleansing composition as defined in claim 5, wherein said anionic surfactant is taken from the group consisting of sulfates, sulfonates, other than the sulfonate of claim 1, sulfoacetates, sulfosuccinates, sarcosines, taurines and isethionates.

8. The personal cleansing composition as defined in claim 6, wherein the ratio of said salt of alcohol ethoxy glyceryl sulfonate to said alcohol ether sulfate is in the range of 1:2 to 1:4.

9. The personal cleansing composition as defined in claim 1, wherein the surfactant is non-ionic surfactant.

10. The personal cleansing composition as defined in claim 9, wherein said non-ionic surfactant is taken from the group consisting of alkanoic acid alkanolamides.

11. The personal cleansing composition as defined in claim 1, wherein the surfactant is a zwitterionic surfactant.

12. The personal cleansing composition as defined in claim 11, wherein said zwitterionic surfactant is cocoamidopropyl betaine.

13. The personal cleansing composition as defined in claim 5, wherein said composition is in the form of a liquid and the amount of said salt of alcohol ethoxy glyceryl sulfonate is in the range of 2 to 25 wt. %.

14. The personal cleansing composition as defined in claim 5, wherein said composition is in the form of a gel and the amount of said salt of alcohol ethoxy glyceryl sulfonate is in the range of 2 to 25 wt. %.

15. The personal cleansing composition as defined in claim 1, wherein said salt of alcohol ethoxy glyceryl sulfonate has a carbon chain length of $C_4$ to $C_{24}$ and has 1 to 10 ethylene oxide units.

16. The personal cleansing composition as defined in claim 5, wherein said composition is in the form of a bar and said anionic surfactant is taken from the group consisting of sulfates, sulfonates, other than the sulfonates of claim 1 sulfoacetates, sulfosuccinates, sarcosines, taurines and isethionates.

17. The personal cleansing composition as defined in claim 3, wherein said soap comprises sodium tallowate and sodium cocoate.

18. A mild skin cleansing bar comprising 1 to 60 wt. % of a surfactant having the formula:

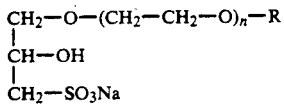

where R is a radical with 4 to 24 carbon atoms and the average value of n is a number from 1 to 10, and further comprising 1 to 85 wt. % of a soap.

19. A mild shampoo composition comprising 2 to 25 wt. % of a surfactant having the formula:

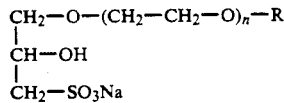

where R is a radical with 4 to 24 carbon atoms and the average value of n is a number from 1 to 10.

20. A mild liquid soap comprising 2 to 25 wt. % of a surfactant having the formula:

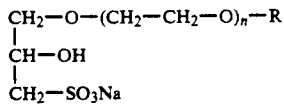

where R is a radical with 4 to 24 carbon atoms and the average value of n is a number from 1 to 10.

21. A mild shower gel comprising 2 to 25 wt. % of a surfactant having the formula:

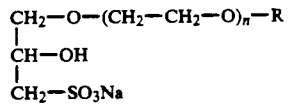

where R is a radical with 4 to 24 carbon atoms and the average value of n is a number from 1 to 10.

22. The personal cleansing composition as defined in claim 3 wherein the soap is at least essentially free of $C_6$-$C_{10}$ hydrocarbons.

23. The personal cleansing composition as defined in claim 19 wherein the soap is at least essentially free of $C_6$-$C_{10}$ hydrocarbons.

24. The personal cleansing composition as defined in claim 19 wherein the sodium cocoate is at least essentially free of $C_6$-$C_{10}$ hydrocarbons.

25. A personal cleansing composition comprising a salt of alcohol ethoxy glyceryl sulfonate and a gum.

26. A personal cleansing composition comprising a salt of alcohol ethoxy glyceryl sulfonate and a polyquaternium.

27. A personal cleansing composition comprising a salt of alcohol ethoxy glyceryl sulfonate and a fragrance.

28. A personal cleansing composition comprising a salt of alcohol ethoxy glyceryl sulfonate wherein the composition is in solid bar form.

29. A personal cleansing composition comprising a salt of alcohol ethoxy glyceryl sulfonate wherein the composition is liquid and is packaged in a container which fits readily in the hand.

30. A method of cleansing the body which comprises applying a personal cleansing composition having a salt of alcohol ethoxy glyceryl sulfonate to the body.

* * * * *